United States Patent [19]

Malé-Brune

[11] Patent Number: 5,660,855
[45] Date of Patent: Aug. 26, 1997

[54] LIPID CONSTRUCTS FOR TARGETING TO VASCULAR SMOOTH MUSCLE TISSUE

[75] Inventor: Roxanne Malé-Brune, Hillsborough, N.C.

[73] Assignee: California Institute of Technology, Pasadena, Calif.

[21] Appl. No.: 386,579

[22] Filed: Feb. 10, 1995

[51] Int. Cl.$^6$ .......................... A61K 9/127; A61K 38/16; A61K 38/00; A61K 31/70
[52] U.S. Cl. ................. 424/450; 514/7.1; 514/9; 514/24
[58] Field of Search ................ 424/450; 514/7.1, 514/9, 24

[56] References Cited

U.S. PATENT DOCUMENTS

| | | | |
|---|---|---|---|
| 4,229,441 | 10/1980 | Bugianesi et al. | 424/182 |
| 4,310,505 | 1/1982 | Baldeschwieler et al. | 424/1 |
| 5,435,989 | 7/1995 | Presant et al. | 424/1.21 |

FOREIGN PATENT DOCUMENTS 9415646  7/1994  WIPO.

OTHER PUBLICATIONS

Mauk, M.R., et al., "Targeting of Lipid Vesicles: Specificity of Carbohydrate Receptor Analogues for Leukocytes in Mice." Proc. Natl. Acad. Sci., vol. 77, No. 8, pp. 4430–4434, Aug. (1980).

Palutz, G.E., et al., "Liposome Mediated Gene Transfer into Vascular Cells", J. Liposome Research 3(2): 179–199 (1993).

Felger, P.L., et al., "Lipofection: A Highly Efficient, Lipid–Mediated DNA–Transfection Procedure", Proc. Natl. Acad. Sci., 84:7413–7417 Nov. (1987).

Morishita, R., et al., "Single Intraluminal Delivery of Antisence cdc2 Kinase and Proliferating–Cell Nuclear Antigen Oligonucleotides Results in Chronic Inhibition of Neointimal Hyperplasia" Proc. Natl. Acad. Sci. 90:8474–8478, Sep. (1993).

Abe, Jun-ichi, et al., "Suppression of Neointimal Smooth Muscle Cell Accumulation In Vivo By Antisense CDC2 and CDK2 Oligonucleotides In Rat Carotid Artery." Biochem & Biophy Research Comm., pp. 16–24, vol. 198, No. 1, Jan. 14, 1994.

Powell, Janet, et al., "Gene Transfer Into Specific Vascular Cells." Eur. Vasc. Surg. 6, 130–134 (1992).

Gershon, Hezi, et al., "Mode of Formation and Structural Features of DNA–Cationic Liposome Complexes Used for Trasfection." Biochemistry, 32 7143–7151 (1993).

Wang, Chen–Yen, et al., "Plasmid DNA Absorbed to pH–Sensitive–Liposomes Efficiently Transforms the Target Cells." Biochem & Biophy Research Communication, vol. 147, No. 3, pp. 980–985, Sep. 30, 1987.

Loke, S.L. et al., "Delivery of c–myc Antisense Phosphorothioate Oligodeoxynucleotides to Hematopoietic Cells In Culture by Liposome Fusion: Specific Reduction in c–myc Protein Expression Correlates with Inhibition of Cell Growth and DNA Synthesis." Microbiology and Immunology, pp. 282–289; vol. 141., (1988).

Lurquin, Paul F., "Entrapment of Genetic Material into Liposomes and Delivery to Cellsl" Liposome Technology, pp. 187–193, vol. 2(1982).

Baldeschwieler, J.D., "Phospholipid Vesicle Targeting Using Synthetic Glycolipid and Other Determinants." Annals New York Academy of Sciences, 446:349–361 (1985).

Jaroszewski, J.W., et al., "Cellular Uptake of Antisense Oligodeoxynucleotides." Advanced Drug Delivery Reviews, 6 235–250, (1991).

Akhtar, Saghir, et al., "Interactions of Antisense DNA Oligonucleotide Analogs with Phospholipid Membranes (Liposomes)." Nucleic Acids Research, vol. 19, No. 20 pp. 5551–5559 (1991).

Bennett, Frank et al., "Cationic Lipids Enhance Cellular Uptake and Activity of Phosphorothioate Antisense Oligonucleotides." Molecular Pharmacology, 41:1023–1033. (1992).

Bone, R.C. ed., "Restenosis after Coronary Angioplasty." Diease–A–Month, 39:616–670 (1993).

Herman, J.P. et al., "Pharmacological Approaches to the Prevention of Restenosis Following Angioplasty, The Search for The Holy Grail?", (parts I and II) Drugs 46(1):18–52, 46(2):249–262, (1993).

Reynolds, Mark A., "Triple–Strand–Forming Methylphosphonate Oligodeoxynucleotides Targeted t mRNA Efficiently Block Protein Synthesis." Proc. Natl. Acad. Sci, U.S.A. vol. 91, pp. 12433–12437, Dec. 1994.

Remy, Jean Serge, "Gene Transfer with Series of Lipophilic DNA–Binding Molecules." Bioconjugate Chem., 5, pp. 647–654 (1994).

Black, Lauren, "Regulatory Considerations for Oligonucleotides Drugs: Updated Recommendatio for Pharmacology and Toxicology Studies." Antisense Research and Development 4:299–301 (1994).

Nagano, et al, Growth inhibition of a gastric cancer cell line by antisense oligonucleotides to c–myc and bcl–2, *Gastroenterology*, 106:A419 (Apr. 1994).

Shi, et al, Maximizing gene transfer into vascular smooth muscle cells, *J. Am. Coll. Cardiology*, 21(2):209 A (1993).

Stewart, et al, Gene transfer in vivo with DNA–liposome complexes: Safety and acute toxicity in mice, *Human Gene Therapy*, 3:267–275 (1992).

*Primary Examiner*—Kimberly Jordan
*Attorney, Agent, or Firm*—NeXstar Pharmaceuticals

[57] ABSTRACT

A lipid construct comprising an aminomannose derivatized cholesterol suitable for targeting smooth muscle cells and tissue. Preferred formulations contain 6-(cholest-5-en-3β-yloxyl)hexyl-6-amino-6-deoxy-1-thio-α-D-mannopyranoside in liposome formulations wherein the formulations are delivered generally to arteries using percutaneous transluminal coronary angioplasty procedures. These formulations have applications in the reduction of restenosis.

8 Claims, 4 Drawing Sheets

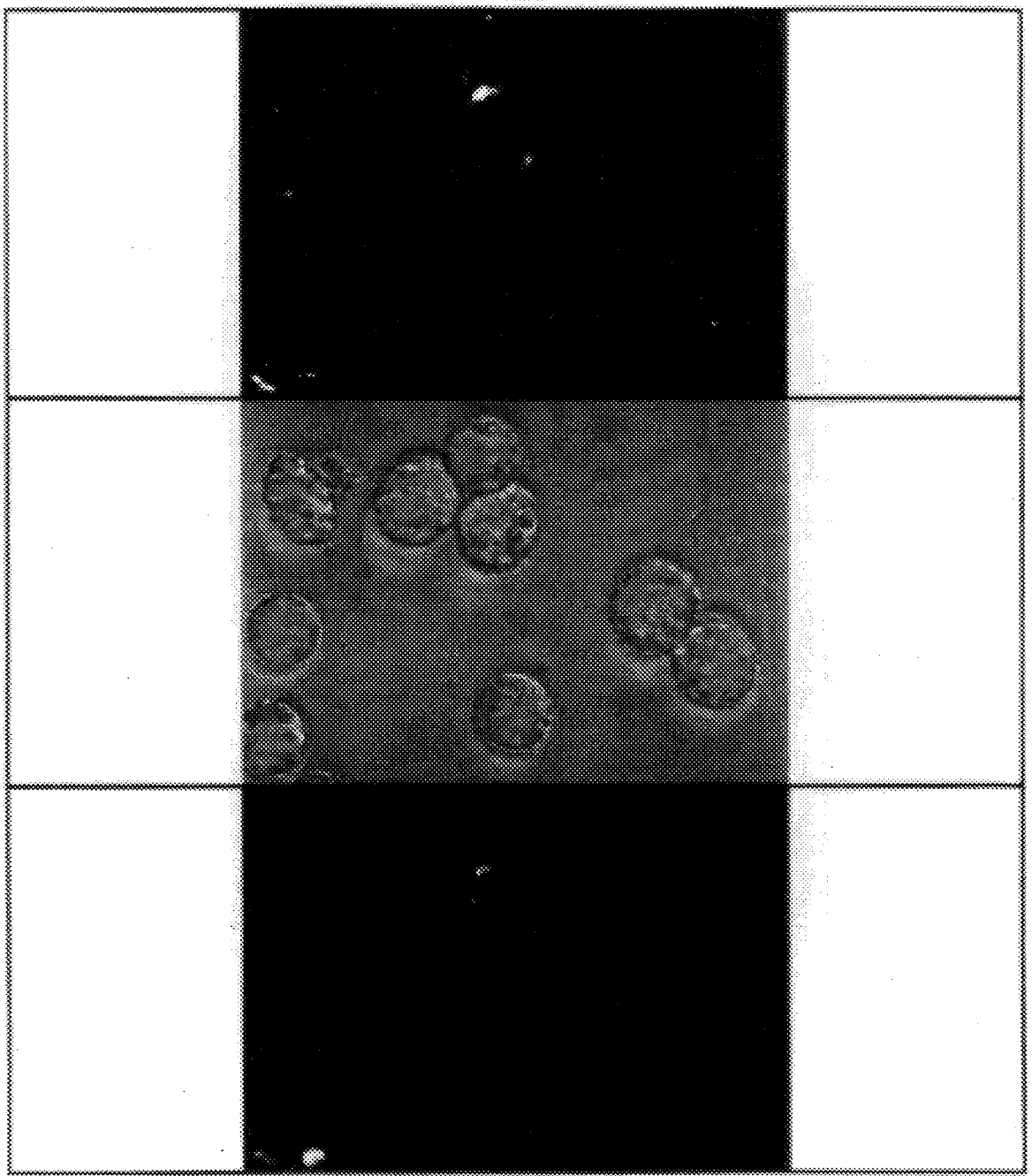

DOPE:Amch:Oligo
at 2.5 hours

DOPE:Amch:Oligo
at 16 hours

DSPC:Chol:Oligo at 2.5 hours

DSPC:Chol:Oligo at 16 hours

LIPID CONSTRUCTS FOR TARGETING TO VASCULAR SMOOTH MUSCLE TISSUE

FIELD OF THE INVENTION

This invention relates generally to pharmaceutical sciences and more particularly to the production of lipid constructs for the delivery of drugs to the cytoplasm of a cell and in particular to vascular smooth muscle tissue. A preferred use of this invention relates to the administration of these constructs for the prevention of restenosis following angioplasty.

BACKGROUND OF THE INVENTION

In order for many drugs and imaging agents to have therapeutic potential it is necessary for them to be delivered to the proper location in the body. In many cases, agents are ineffective because it is impossible, with the available technology, to deliver them to the proper locations within a biological organism. Thus, a main focus in pharmaceutical research is in the delivery of agents to tissues and cells.

An area of development aggressively pursued by researchers is in the delivery of agents not only into a cell but into the cell's cytoplasm and further yet, into the nucleus. This area of research is being pursued in particular for delivery of biological agents such as DNA, RNA, ribozymes and proteins. Not only do these materials hold great promise as therapeutic agents, but some workers believe that in some diseases they may act as the "magic bullet" i.e., curing an illness without deleterious side effects. Examples of therapeutic pursuits include the application of antisense technology. Briefly, the strategy in antisense technology is to deliver an agent such as DNA oligonucleotide that binds to sites on messenger RNA (mRNA) which directs the production of proteins related to disease. Other strategies include the use of triplex agents which bind to the double helix to interfere with transcription, preventing the production of mRNA. In spite of these developments, numerous "delivery" problems have surfaced.

One major problem encountered is that effective delivery of oligonucleotides across cell membranes is difficult, if not impossible. Another problem facing workers is that oligonucleotides are degraded by intracellular and extracellular enzymes such as exonucleases and endonucleases. In order to overcome these problems, workers have modified the typical phosphodiester form of oligonucleotides. For example, modifications have included the creation of phosphorothioate and methylphosphonate oligonucleotides. Methylphosphonate oligonucleotides contain uncharged sectors which increase intracellular uptake and resist enzymatic degradation. Phosphonothioate oligonucleotides are negatively charged but are resistant to endonucleases. Although these modified oligonucleotides show promise as therapeutics, there is no evidence of in vivo success. Further, workers have not provided a delivery vehicle capable of introducing a sufficient quantity of oligonucleotides into the cell such that it has therapeutic effect. Since it is desirable to load a cell with s numerous oligonucleotides, workers have begun to focus their efforts on developing a delivery vehicle which not only acts to deliver an agent into the cytoplasm and nucleus of a cell, but also delivers oligonucleotides in large numbers.

Cationic liposomes have been used to introduce DNA into vascular cells. Plautz, G. E., et al, "Liposome Mediated Gene Transfer into Vascular Cells", *J. Liposome Research* 3(2):179–199 (1993); Felgner, P. L., et al. "Lipofection: A highly efficient, lipid-mediated DNA-transfection procedure", *Proc. Natl. Acad. Sci.* 84:7413–7417 (1987). For example, Lipofectin, liposomes formed from a mixture of N-[2,3-(dioleyloxy)propyl]-N,N,N-trimethylammonium chloride (DOTMA) and dioleoylphosphatidylethanolamine (DOPE), has been used to transduce recombinant genes into coronary arteries in vivo. Another example of a cationic liposome used to introduce genes into DNA is a liposome preparation containing DC-chol, 3b[N-(9N'N'-dimethylaminoethane)-carbamoyl] cholesterol and DOPE. Other efforts have been directed toward the use of modified retroviruses and cationic liposomes for gene transfer.

Liposomes in general have been known. Liposomes are microscopic vesicles made from phospholipids, which form closed, fluid filled spheres when dispersed with aqueous solutions. Phospholipid molecules are polar, having a hydrophilic head and two hydrophobic tails consisting of long fatty acid chains. Thus, when a sufficient concentration of phospholipid molecules are present in aqueous solutions, the tails spontaneously associate to exclude water while the hydrophilic phosphate heads interact with water. The result is a spherical, bilayer membrane in which the fatty acid tails converge in the interior of the newly formed membrane, and the polar heads point in opposite directions toward an aqueous medium. These bilayer membranes thus form closed spheres, known as liposomes. The polar heads at the inner surface of the membrane point toward the aqueous interior of the liposome and, at the opposite surface of the spherical membrane, the polar heads interact with the surrounding aqueous medium. As the liposomes are formed, water soluble molecules can be incorporated into the aqueous interior, and lipophilic molecules may be incorporated into the lipid bilayer. Liposomes may be either multilamellar, like an onion with liquid separating many lipid bilayers, or unilamellar, with a single bilayer surrounding an aqueous center.

Methods for producing liposomes are well known in the art, and there are many types of liposome preparation techniques which may be employed to produce various types of liposomes. These can be selected depending on the use, the chemical intended to be entrapped, and the type of lipids used to form the bilayer membrane. The requirements which must be considered in producing a liposome preparation are similar to those of other controlled release mechanisms. They are: (1) a high percent of chemical entrapment; (2) increased chemical stability; (3) low drug toxicity; (4) rapid method of production; and (5) a reproducible size distribution.

The first method described to encapsulate drugs or other chemicals in liposomes involved the production of multilamellar vesicles (MLVs). Liposomes can also be formed as unilamellar vesicles (UVs), which generally have a size less than 0.5 μm (μm, also referred to as "microns"). There are several techniques known in the art which are used to produce unilamellar liposomes.

Smaller unilamellar vesicles can be formed using a variety of techniques, such as applying a force sufficient to reduce the size of the liposomes and or produce smaller unilamellar vesicles. Such force can be produced by a variety of methods, including homogenization, sonication or extrusion (through filters) of MLVs. These methods result in dispersions of UVs having diameters of up to 0.2 μm, which appear as clear or translucent suspensions. Other standard methods for the formation of liposomes are know in the art, for example, methods for the commercial production of liposomes include the homogenization procedure described in U.S. Pat. No. 4,753,788 to Gamble, a preferred technique, and the method described in U.S. Pat. No. 4,935,171 to Bracken, which are incorporated herein by reference.

Another method of making unilamellar vesicles is to dissolve phospholipids in ethanol and injecting them into a buffer, whereby the lipids will spontaneously rearrange into unilamellar vesicles. This provides a simple method to produce UVs which have internal volumes similar to that of those produced by sonication (0.2–0.5 L/mol of lipid). Another common method for producing small UVs is the detergent removal technique. Phospholipids are solubilized in either ionic or non-ionic detergents such as cholates, Triton X-100, or n-alkylglucosides. The drug is then mixed with the solubilized lipid-detergent micelles. Detergent is then removed by one of several techniques: dialysis, gel filtration, affinity chromatography, centrifugation or ultrafiltration. The size distribution and entrapment efficiencies of the UVs produced this way will vary depending on the details of the technique used.

The therapeutic uses of liposomes include the delivery of drugs which are normally toxic in the free form. In the liposomal form the toxic drug may be directed away from the sensitive tissue and targeted to selected areas. Liposomes can also be used therapeutically to release drugs, over a prolonged period of time, reducing the frequency of administration. In addition, liposomes can provide a method for forming an aqueous dispersion of hydrophobic drugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body. The route of delivery of liposomes can also affect their distribution in the body. Passive delivery of liposomes involves the use of various routes of administration, e.g., intravenous, subcutaneous and topical. Each route produces differences in localization of the liposomes. Two methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Furthermore, since liposomes are essentially hollow spheres made up of amphipathic molecules, they can entrap hydrophilic drugs in their aqueous interior space and hydrophobic molecules in their lipid bilayer. Unwanted molecules that remain in the dispersion external to the liposomes, such as unentrapped agents, are removed by column chromatography or ultrafiltration. Although methods for making liposomes are well known in the art, it is not always possible to determine a working formulation without experimentation.

U.S. Pat. No. 4,310,505, incorporated by reference, discloses lipid vesicle formulations containing amino sugar derivatives of cholesterol as cell-surface receptor analogs. The vesicles were found to release their contents in a controlled manner, and in some cases, to be rapidly concentrated in the lymphatic system and/or liver, lungs or spleen of the host. These liposomes were noted to be used in the treatment of lysosomal storage disease. Liposomes containing amino-sugar derivatives have been shown to localize in s aggregates of polymorphonuclear leukocytes. Mauk, M. R. et al., "Vesicle Targeting: Timed Release and Specificity for Leukocytes in Mice by Subcutaneous Injection" Science 207:309–311 (1980).

The delivery problems noted above become manifest in treating a disease such as arteriosclerosis, a disease associated with the hardening or narrowing of arterial walls and the leading cause of death in Western Society. The majority of these deaths is caused by atherosclerosis, a type of arteriosclerosis characterized by lipid deposits in the intima of large and medium size arteries. These deposits or lesions are typically classified as fatty streaks, fibrous plaques or complicated lesions. Fatty streaks, probably the earliest lesions of atherosclerosis, are generally characterized by a build-up of lipid-filled smooth muscle cells, macrophage and fibrous tissue in the intima. Advanced atherosclerosis gives rise to fibrous plaques, which are raised lesions and elevated areas of intimal thickening. These lesions consist of a central core of extracellular lipid and necrotic cell debris (gruel) covered by a fibromuscular layer containing large numbers of smooth muscle cells, macrophage, and collagen. The third class, known as the complicated lesion, is characterized by calcified fibrous plaques. Stenosis, or narrowing, of vascular passages can result from gradual occlusion as the plaques thicken and thrombi form.

Atherosclerosis and stenotic vascular lesions are typically treated through the use of percutaneous transluminal coronary angioplasty (PTCA) procedures. These methods, which include balloon angioplasty, the atherectomy catheter, the excimer laser, and the rotablator, are used to dilate the stenosed blood vessels. However, the efficacy of PTCA is limited by the development of restenosis, or renarrowing, of the treated area following PTCA due to neointima formation. Approximately 25% of successful first-time angioplasty procedures must be repeated within 6 months and an additional 10% of the patients must later undergo coronary bypass surgery because of restenosis. A discussion of the causative elements of restenosis appears in Bone, R. C., ed., "Restenosis after Coronary Angioplasty," *Disease-A-Month*, 39:616–670 (1993).

PTCA procedures often cause collateral injury to the arterial wall, which triggers a "healing" process involving a series of physiologic events that ultimately results in neointima formation. Neointima formation is a multi-step process involving a complex interaction among several growth factors which promote vascular smooth muscle cell (VSMC) proliferation and migration. In this process, erosion of the intima, the single continuous layer of endothelial cells lining the arterial walls, during angioplasty promotes platelet aggregation. The platelets adhere to the arterial wall and release growth factors (e.g., platelet-derived growth factor, thrombin, basic fibroblast growth factor and transforming growth factor) which initiate the migration of VSMC to the intima and promote the proliferation of VSMC comprising the tunica media. Growth factor-induced VSMC proliferation involves, in turn, a sequential activation of intracellular proteins which promote cell-cycle progression. The next step of the process is associated with an inflammatory response, evidenced by an invasion of inflammatory cells such as monocytes, macrophage, and other white blood cells. These inflammatory cells further induce and stimulate growth of VSMC in the media, which subsequently migrate into the intimal space and produce large amounts of extracellular proteoglytic matrix material, forming a neointima layer which represents the lesion. It appears that endothelium then grows over the injured area and restenosis results.

Considerable research has been undertaken to identify agents which prevent or reverse restenosis. For example, many agents have been examined in the prevention of restenosis. A comprehensive review of therapeutics potentially useful in the treatment of restenosis appears in Herrman, Jean-Paul R. et al. "Pharmacological Approaches to the Prevention of Restenosis Following Angioplasty, The Search for The Holy Grail?" (parts I and II) *Drugs* 46 (1): 18– 52, 46 (2):249–262, 1993.

Other drugs considered for inhibiting restenosis include, but are not limited to, oligonucleotides (e.g., antisense gene therapy), protein kinase C, endothelial growth factor and anti-platelet activating agents. Efforts to prevent restenosis utilizing systemic administration of such drugs, however, have been hampered by generalized toxicity at effective dosages. Furthermore, successful therapy for preventing restenosis has been thwarted by the complexity of the physiological processes responsible for neointima formation as well as the inability to deliver effective quantities of drugs to the site of injury, due to inefficient cellular uptake and lack of specificity (i.e., targeting) to VSMC. One possible mechanism for the failure of drugs to provide effective prevention of restenosis is that the agents never reach the tissue targeted. For example, the candidate agents may simply be washed away from the treatment areas by blood flow.

Gene therapy, using antisense oligonucleotides which effectively "shut off" the genes involved in neointima formation, is a promising approach to the problem of restenosis. However, due to the multiplicity of growth factors involved in neointima formation, selective inhibition of any single growth factor is unlikely to completely prevent lesion formation. Accordingly, Morishita has shown inhibition of neointima hyperplasia in a rat carotid model following angioplasty injury by administration of two antisense oligonucleotides (AS-oligos) which block the cell-cycle regulatory genes for proliferating-cell nuclear antigen (PCNA) and $p34^{cdc2}$ (cdc2). Morishita, R. et al. "Single intraluminal delivery of antisence cdc2 kinase and proliferating-cell nuclear antigen oligonucleotides results in chronic inhibition of neointimal hyperplasia" *Proc. Natl. Acad. Sci.* 90:84774 (1993). PCNA, a nuclear protein required for DNA synthesis by DNA polymerase Δ, and cdc2, a serine/threonine protein kinase, are primary components of the cell-cycle progression which regulate VSMC proliferation. The AS-oligos were constructed to be directed to the translation initiation sites of PCNA and cdc2. Cellular uptake was enhanced and transfection stability of the AS-oligos increased by complexing the phosphorothioate AS-oligos with liposomes and the protein coat of inactivated Sendai hemagglutinating virus of Japan (HVJ). Morishita et al. observed more rapid uptake and a 10-fold increase in transfection efficiency of AS-oligos or plasmid DNA than standard lipofection or passive uptake methods. However, specific targeting of the HVJ AS-oligos liposome complex to VSMC was not reported. It is generally desired then to develop targeting specificity of drug carriers to VSMC since that would result in greater uptake by the smooth muscle cells at the site of injury and would permit the administration of higher, more effective dosages. Furthermore, it is advantageous to avoid the use of viral proteins in drug carriers as they present a potential biological hazard to humans.

Thus, it is an object of the present invention to provide a lipid construct that is superior and more effective in delivering agents into the cytoplasm and nucleus of a cell. It is yet another object of the present invention to provide for the targeting of an agent to vascular smooth muscle tissue. It is still yet a further object of this invention to provide for a less toxic and more efficacious treatment of such diseases as restenosis, viral diseases and cancer.

SUMMARY OF THE INVENTION

The invention provides for the delivery of an imaging or therapeutic agent into the cytoplasm of a cell by delivering the lipid construct to a mammal wherein the lipid construct comprises an aminomannose derivatized cholesterol. The delivery of the agents could be done in vitro as well as in vivo. This includes delivery of agents to cells, tissues or organs in vitro and reintroduction of the cells, tissues or organs in vivo. It also includes the transfection of cultured cells in vitro for the purpose of conferring desireable properties in these cells, including enhanced, decreased or novel production of proteins.

Lipid constructs, for purposes of this invention, are complexes containing lipids, phospholipids, or derivatives thereof comprising a variety of different structures which lipids are known to adopt in aqueous suspension. These structures include, but are not limited to, micelles, liposomes, lipid ribbons or sheets, and may be complexed with a variety of drugs and adjuvants which are known to be pharmaceutically acceptable. Common adjuvants include cholesterol and α-tocopherol, among others. The lipids may be used alone or in any combination which one skilled in the art would appreciate to provide the characteristics desired for a particular application. In addition, the technical aspects of lipid complex and liposome formation are well known in the art and any of the methods commonly practiced in the field may be used for the present invention.

The present invention further comprises a method for targeting vascular smooth muscle tissue and cells comprising the delivery of an agent, to the cell using a lipid construct comprising an aminomannose derivatized cholesterol. This approach is advantageous over the prior art since it provides targeting but does not involve the use of viral products. The aminomannose-containing lipid constructs exhibit dramatically enhanced in vitro and in vivo targeting to Vasecular Smooth Muscle Cells (VSMC) compared to identical constructs not containing aminomannose. While we do not wish to be bound by any particular theory, it appears that the increased targeting results from specific mannose-receptor-mediated endocytosis or fusion of the lipid constructs. In another aspect of the invention, the lipid constructs contain drugs which inhibit neointima formation and are administered to prevent restenosis following PTCA procedures. Since restenosis is caused generally from the accumulation of VSMC, the targeting of such cells is critical during PCTA procedures.

Also provided herein is a method of delivering a lipid compound into a vascular smooth muscle cell by delivering a lipid construct to a mammal comprising aminomannose derivatized cholesterol.

The preferred composition for carrying out the invention includes a lipid construct comprising an aminomannose derivatized cholesterol. Further embodiments of the invention include the construct having a cationic lipid wherein the total cationic lipid is greater than or equal to 5% of total lipid and the lipid construct further comprises a therapeutic or imaging agent. The aminomannose derivatized cholesterol is included in the definition of a cationic lipid.

The invention is useful for inhibiting restenosis in a mammal by delivering a lipid construct to the mammal wherein the lipid construct comprises an aminomannose derivatized cholesterol and a cationic lipid wherein the total cationic lipid is greater than or equal to 5% of total lipid wherein the lipid construct further comprises an agent in an amount effective for said inhibition. The 5% cationic lipid could include only aminomannose derivatized cholesterol.

Another aspect of the invention comprises the cytoplasmic delivery of an agent into the cytoplasm of a cancer cell.

BRIEF DESCRIPTION OF THE DRAWINGS

FIG. 2 shows a confocal micrograph of fluorescently labeled chimeric oligonucleotide taken at 2.5 hours.

DETAILED DESCRIPTION OF THE INVENTION

The present invention relates to the formation of a lipid construct comprising a aminomannose derivatized cholesterol. A preferred representative of this compound is 6-(cholest-5-en-3β-yloxy)hexyl-6-amino-6-deoxy-1-thio-α-D-mannopyranoside (Amch).

Of course any number of lipids may be used in combination with aminomannose derivatized cholesterol. Examples of lipids which may be used successfully include: dimyristoyl triethylamine propane (DMTAP), dimyristoyl dimethylammonium propane (DMDAP), 1,2-dioleoyl-3-trimethylammonium propane (DOTAP), 1,2-dioleoyl-3-dimethylammonium propane (DODAP) and dioleoyl-sn-glycero-3-ethylphosphatidylcholine (DGE), hydrogenated soy and egg phosphatidyl choline (HSPC, HEPC) distearoyl phosphatidylcholine (DSPC), dimyristoylphosphhtidylcholine (DMPC), dilaurylphospatidycholine (DLPC), dioleylphosphatidylcholine (DOPC), phosphatidylethanolamine (PE), dimyristoylphosphatidylethanolamine (DMPE), dioleoylphosphatidylethanolamine (DOPE), cholesterol, N-[2,3-(dioleyloxy)propyl]-N,N,N-trimethylammonium chloride (DOTMA), 3b[N-(N'N'-dimethylaminoethane)-carbamoyl] cholesterol (DC-Chol). These lipid constructs may also be used to treat or prevent cancer or viral infections by facilitating delivery of oligonucleotide therapeutic agents to the cellular cytoplasm.

Figure 1:
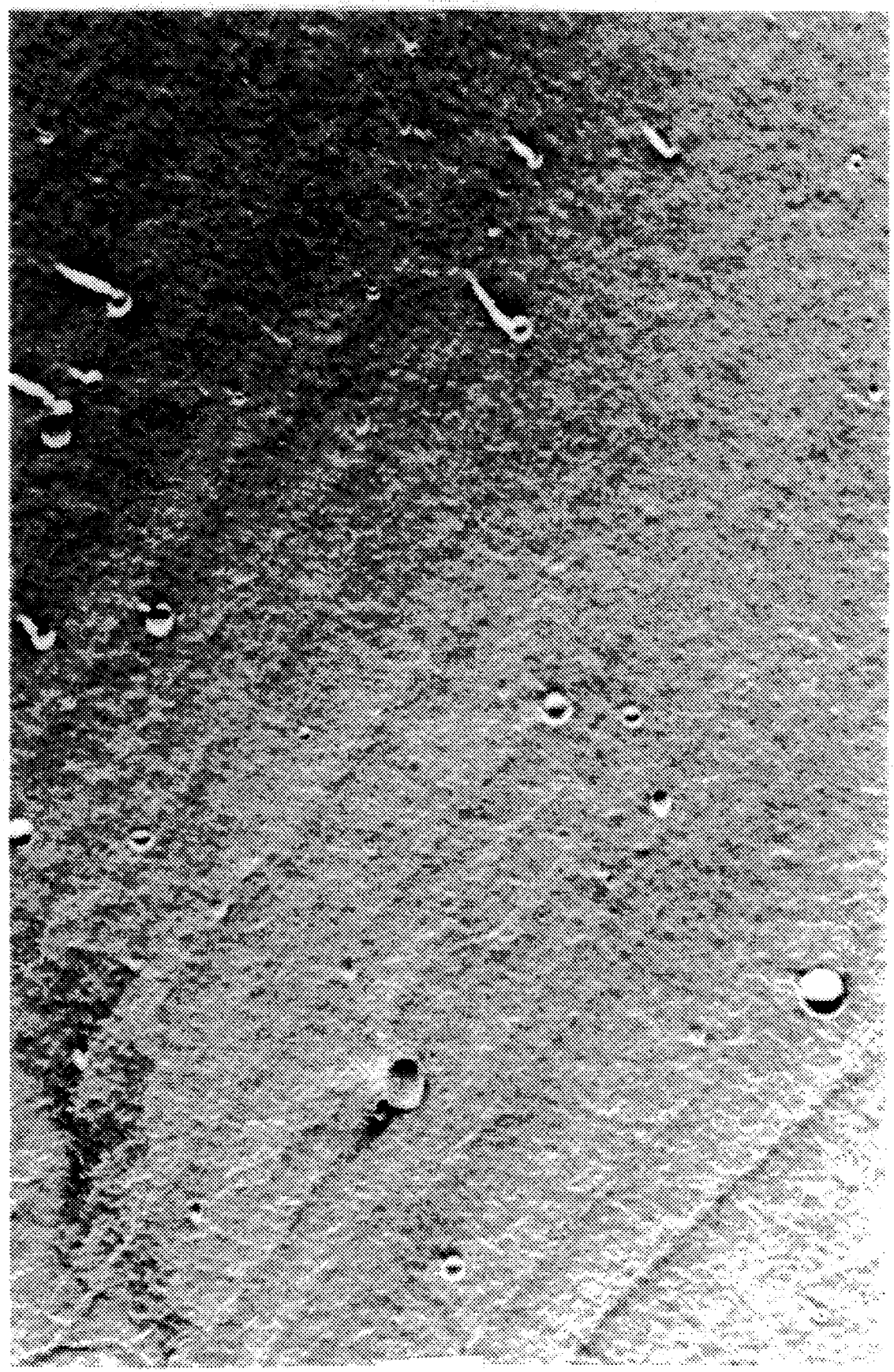
FIG. 1 shows a freeze fracture micrograph of a lipid construct-containing oligonucleotides.

These lipids may be used in any suitable combination with an aminomannose derivatized cholesterol. Preferred lipid formulations are listed in Tables 1 & 2. The following formulations give rise to optimal results in preventing restenosis: DOPE:Amch (1:1 molar ratio) having a lipid to oligonucleotide ratio (w/w) less than 5:1 and preferably between 1.25:1 & 0.5:1. The preferred size of these constructs range from 10 nm to 250 nm preferably at 50 nm. Preferred lipids used in the constructs comprise cationic lipids, preferably greater than or equal to 5% total lipid. The preferred lipid construct is a unilamellar liposome as shown in FIG. 1 wherein the liposome is prepared having a formula DOPE:Amch (1:1 molar ratio).

The lipid constructs preferred for use in delivering oligonucleotides which inhibit tumor growth comprise HSPC:Chol:Amch in a mole ratio of 16:8:1.

The preferred lipid constructs are prepared by first hydrating a mixture of lipids in suitable buffer such as 9% sucrose. Prior to hydration, it is preferable that a lipid powder or film is formed of the lipid mixture, for example, by spray-drying or rotary evaporative techniques.

One preferred use of the invention is in the treatment of restenosis, and further for the prevention of neointima formation. Agents that may be used include the following: antithrombotic agents, antiplatelet agents, antiproliferative agents, anti-inflammatory agents, calcium antagonists, lipid lowering drugs, and antibodies to growth factors, inositol diphosphate, and antisense compounds. Some of these agents include coumadin, heparin, low molecular weight heparins, hirudin, aspirin, dipyridamole, thromboxane A2, thromboxane A2 synthetase inhibitor, thromboxane A2 receptor blockers, ridogrel, sulfinpyrazone, dextran, prostacyclin or prostacyclin analogues, prostaglandin E1, ticlopidine, serotonin antagonists, glycoprotein IIb/IIIa receptor blockers, angiotensin converting enzyme inhibitors, colchicine, platelet-derived growth factor antagonists, angiopeptin, somatomedin, octreotide, cytostatic, corticosteroids, ibuprofen, nifedipine, nicardipine, diltiazem, verapamil, fish oils, (such as omega 3 fatty acids, eicosapentaenoic acids, and docosahexaenoic acids), lovastatin, postangioplasty, colestipol, and antibodies. Microparticles have been noted as a potential microcarrier drug delivery system in order to prevent the rapid elimination by the increased network of vasa vasorum and atherosclerotic lesions that cause early outward diffusion. Red blood cells have also been investigated as a microcarrier system.

The preferred agents used are oligonucleotides that inhibit neointima formation and prevent restenosis. The preferred size of the oligonucleotide, is from 15 mer to 30 mer although sizes up to 80 mer may be associated with the lipid construct taught in this invention.

The present invention is also useful for blocking cell-cycle regulatory genes such as proliferating-cell nuclear antigen (PCNA), p34cdc2 (cdc2), and cdk2 (cyclin-dependent kinases). Antisense oligonucleotides directed toward translation sites of these genes provide optimum results. In the treatment of cancer, such antisense oligonucleotides corresponding to the bcl-2 or c-myc mRNA provide significant benefits.

This invention has particular advantages for complexing aminomannose derivatized cholesterol with ligands generated by the SELEX® technology as described in U.S. Pat. No. 5,270,163 and incorporated herein by reference.

This invention will be more fully understood by reference to the following examples, which are intended to be illustrative of the invention, but not limiting thereof.

EXAMPLE 1

Liposomal Targeting and Uptake of Smooth Muscle Cells

A. Preparation of Liposomes

Two liposome formulations were prepared. A lipid film containing distearoyl phosphatidylcholine (DSPC) and cholesterol (Chol) in a 2:1 molar ratio was prepared. A second lipid film containing DSPC, Chol and aminomannose derivatized cholesterol (Amch) in a molar ratio of about 2:0.96:0.04 was also prepared. The lipid films were formed by dissolving the lipids in chloroform, mixing and then evaporating off the chloroform. The lipid films were radiolabeled with $^3$H-cholesteryl hexadecyl ether and/or fluorescently labeled with the lipophilic fluorescent probe, octadecyl rhodamine. The $^3$H-cholesterylhexadecyl ether (5 μCi) was added during the formation of the lipid film. The lipids were hydrated in 100 mM NaCl and 25 mM phosphate buffer pH 7.4 and probe sonicated for approximately 10 minutes to form unilamellar vesicles with an average diameter of 70 nm±20 nm. The octadecyl rhodamine was incubated with the liposomes for 20 minutes to fluorescently label the liposomes.

B. In Vitro Measurement of Uptake by Smooth Muscle Cells

The $^3$H-cholesterylhexadecyl ether labeled liposomes were incubated with confluent rat aortic vascular smooth muscle cells for 5, 30, and 60 minutes. The uptake of the liposomes was measured by scintillation counting and reported in Table 1 as counts per minute (cpm) per microgram of cell protein. All time points were done in triplicate. Fluorescence microscopy and autoradiography were performed to qualitatively detect the association of the liposomes with the vascular smooth muscle cells.

TABLE 1

Uptake of Labeled Liposomes by Vascular Smooth Muscle Cells In CPM/μG Protein

|  | 0' | 5' | 30' | 60' |
|---|---|---|---|---|
| DSPC:Chol | 1.35 | 3.63 | 4.22 | 6.51 |
| DSPC:Chol:Amch | 1.22 | 25.17 | 40.35 | 52.53 |

C. In Vivo Measurement of Uptake by Smooth Muscle Cells

White New Zealand rabbits were anesthetized and both femoral arteries were exposed. A balloon catheter was advanced into the iliac artery through a cut-down of the femoral artery. The catheter consisted of a metallic plate and tubular extrusions (delivery nipples) occupying one third the circumference of a balloon. The delivery nipples of the balloon deepened about 0.1 mm into the arterial wall. The balloon of the catheter was inflated to 1.5 atm. One ml of aminomannose liposomes was delivered into the catheter against the vessel wall with 100 psi within three seconds. Both iliac arteries were used in all animals. The rabbits (6 arteries/group) were sacrificed at 0.5, 1, 4, 24 and 168 hours. Rabbits injected with normal saline or octadecyl rhodamine served as controls (4 arteries/group). The iliac arteries were snap frozen in liquid nitrogen and the rhodamine fluorescence was measured using an Olympus fluorescence microscope.

At thirty minutes the liposomes were accumulated under the adventitia. At four hours, the liposomes began to distribute in the medial layer. At twenty-four hours, the liposomes were distributed in a heavy homogeneous pattern throughout the width of the arterial wall. At one week, the intima remained stained and the liposomes were redistributed into the adventia with the media being clear. The blood vessels of rabbits are somewhat peculiar in that the intima is extremely thin. Therefore, any intima seen after catheterization is assumed to be neointima, formed as a result of migration of VSMC from the media and consequent release of extracellular matrix. By 24 hours, the liposomes redistribute throughout the vessel. At one week the fluorescent dye is clearly seen within the neointima and not the media. Liposomes associated with VSMC within the media migrated across the internal elastica into the neointima.

The above examples establish that lipid constructs comprising an aminomannose derivatized cholesterol target vascular smooth muscle cells (VSMC). Continuing fluorescence microscopy confirmed delivery of the lipid construct to VSMC, evidenced by binding of aminomannose derivatized liposomes to the VSMC tissue. Autoradiography confirmed delivery into VSMC, evidenced by intracellular localization of the lipid within the VSMC.

EXAMPLE 2

Liposomes containing greater than 5% cation lipid were prepared. The lipids were hydrated in sterile-filtered 9% sucrose, heated for 0.5 minutes at 65° C. and sonicated. Sizing was done by microtrac analysis. Oligonucleotides (2328) GTCCTCCATAGTTACTCA (SEQ ID NO:1), (2342) GATCAGGCGTGCCTCAAA (SEQ ID NO:2), (2616) ACTCATTGATACCTCCTG (SEQ ID NO:3) and (2617) AAACTCCGTGCGGACTAG (SEQ ID NO:4) were added to the liposomes and heated at 65° C. for 10 minutes. Table 2 lists all cationic formulations, lipid concentrations and liposome sizes.

TABLE 2

CATIONIC FORMULATIONS

| Formulation#* | Lipid Conc. (mg/mL) | Size (μm) |
|---|---|---|
| DOTAP:DOPE:Amch (1:1:0.5) | 1 | 0.1296 ± 0.1446 |
| DODAP:DOPE:Amch (1:1:0.5) | 1 | 1.2961 ± 1.0803 (34%) |
|  |  | 0.0450 ± 0.0434 (66%) |
| DOPE:Amch (1:1) | 1 | 0.8619 ± 0.6654 (17%) |
|  |  | 0.0942 ± 0.1699 (83%) |
| DMPE:Amch (1:1) | 1 | 0.2734 ± 0.1955 (44%) |
|  |  | 0.0719 ± 0.0604 (58%) |
| DGE:DOPE:Amch (1:1:0.5) | 1 | 2.10 ± 0.482 (35%) |
|  |  | 0.0435 ± 0.044 (65%) |
| DGE:DOPE:Amch (1:1:0.5) | 1 | 1.4785 ± 0.5654 (60%) |
|  |  | 0.1566 ± 0.1430 (20%) |
|  |  | 0.0403 ± 0.0230 (20%) |
| DOPE:Amch (1:1) | 1 | 0.8325 ± 0.7217 (39%) |
|  |  | 0.0594 ± 0.1035 (61%) |
| DMPE:Amch (1:1) | 1 | 1.5735 ± 0.6965 (18%) |
|  |  | 0.0547 ± 0.0917 (82%) |
| DMPE:Amch (1:1.5) | 1 | 1.0709 ± 0.3329 (20%) |
|  |  | 0.0445 ± 0.0445 (74%) |
|  |  | 0.0092 ± 0.0019 (6%) |
| DOPE:Amch (1:1) | 2.85 | 0.0375 ± 0.0510 |
| DMTAP:DMPE:Amch (1:1:0.5) | 3.1 | 0.0158 ± 0.0261 |
| DMDAP:DMPE:Amch (1:1:0.5) | 3.1 | 1.6531 ± 1.1338 (5%), |
|  |  | 0.3152 ± 0.2193 (18%) |
|  |  | 0.0551 ± 0.0542 (77%) |
| DMTAP:DMPE:Amch (1:1:1) | 3.1 | 1.7614 ± 0.5416 (1%) |
|  |  | 0.0123 ± 0.0090 (99%) |
| DOPE:Amch (1:1) | 2.85 | 0.0431 ± 0.0437 (60%) |
|  |  | 0.0218 ± 0.0053 (19%) |
|  |  | 0.0116 ± 0.0020 (21%) |
| DOPE:Amch (1:1) | 3.1 | 1.1795 ± 0.5194 (2%) |
|  |  | 0.0416 ± 0.0761 (98%) |
| DOTAP:DOPE:Amch (1:1:1) | 3.72 | 0.2333 ± 0.1677 |
| DODAP:DOPE:amino (1:1:1) | 3.72 | 0.888 ± 0.5061 (11%) |
|  |  | 0.1172 ± 0.0988 (59%) |
|  |  | 0.0437 ± 0.0179 (30%) |
| DOPE:Amch (1:1) | 3.1 | 0.0438 ± 0.0719 |
| DcChol:DOPC:Amch (0.25:1:0.25) | 4.8 | 0.3135 ± 0.1055 (2%) |
|  |  | 0.0446 ± 0.0603 (96%) |
| DcChol:DOPC (0.5:1) | 2.5 | 1.1016 ± 1.6545 (30%) |
|  |  | 0.0437 ± 0.0469 (70%) |
| DcChol:DOPE:Amch (0.5.1:0.5) | 3.1 | 0.0327 ± 0.0534 |
| DcChol:DOPE (1:1) | 2.7 | 1.5865 ± 0.4214 (24%) |
|  |  | 0.0414 ± 0.0301 (27%) |
|  |  | 0.0095 ± 0.0018 (49%) |
| DOTAP:DOPE:Amino (1:1:0.5) | 3.1 | 0.0496 ± 0.0508 |
| DOPE:Amino (1:1) | 4.65 | 0.0428 ± 0.0718 |
| DOPE:Amino (1:1.5) | 3.0 | 1.4996 ± 0.4880 (12%) |
|  |  | 0.0522 ± 0.0840 (88%) |
| DOTAP:DOPE:Amch (1:1:1.5) | 3.0 | 1.6306 ± 0.8100 (13%) |
|  |  | 0.0343 ± 0.0512 (87%) |
| DOTAP:DOPE:Amch (1.3:1:1.2) | 3.0 | 1.9534 ± 0.7815 (14%) |
|  |  | 0.0541 ± 0.0867 (86%) |
| DOPE:Amch (1:1.2) | 3.1 | 0.3203 ± 0.2097 (7%) |
|  |  | 0.0396 ± 0.0407 (93%) |
| DOTAP:DOPE:Amch (1:1:1.5) | 3.1 | 0.0417 ± 0.0363 |
| DOPE:Amch (1:1) | 3.1 | 0.0622 ± 0.0783 |
| DOSPA:DOPE:Amch (3:1:0.5) | 0.75 | 1.0169 ± 0.2413 |
| DOTMA:DOPE:Amch (1:1:0.5) | 0.8 | 0.0953 ± 0.1004 |

Typically, liposomes were sonicated until greater than 85% of the liposomes were less than 300 nm diameter. This allowed sterile filtration using a 450 nm cellulose acetate filter without significant liposome loss on the filter. All liposome formulations except DOTAP:DOPE:Amch (1:1:1), DODAP:DOPE:Amch (1:1:1) and DOSPA:DOPE:Amch were 10–100 nm average diameter. DOTAP:DOPE- :Amch (1:1:1) and DODAP:DOPE:Amch(1:1:1) averaged 100–200 nm diameter; DOSPA:DOPE:Amch were greater than 1 μm and could not be sterile filtered.

EXAMPLE 3

Lipid constructs were prepared as in Example 2. Electron microscopy was obtained of liposomes prepared with DOPE:Amch (1:1, mole ratio) and mixed with oligonucleotides (2520, SEQ ID NO:5) in a 5:1 lipid:oligo ratio and immediately frozen (FIG 1). FIG. 1 clearly indicates that unilamellar liposomes are formed (magnified 60,000× (1 cm=167 nm)) with an average size of 62±51 nm. Two 21-mer phosphorothioate oligonucleotides targeted to the CAT gene were complexed (and combined), with the lipid construct. The sequences of the oligonucleotides were (2520) TAGCTTCCTTAGCTCCTGCAT (SEQ ID NO:5) and (2519) TAGCTT CCGCAACTCTTGCAT (SEQ ID NO:6), both antisense to a mRNA which code for chloramphenicol acetyl transferase (CAT). Incorporation of the oligos into the cytoplasm should inhibit CAT activity for the proper plasmid only if it is a specific antisense effect. The extent of restenosis inhibition was determined using either of two methods: a chloramphenicol acetyl transferase (CAT) assay or a PCNA/cdc2 assay. Chloramphenicol is an antibiotic which blocks protein synthesis by inhibiting the peptidyl transferase activity of the 50 S ribosomal subunit in prokaryotes; peptidyl transferase catalyzes the formation of peptide bonds. CAT is a bacterial drug-resistance gene which inactivates chloramphenicol by acetylating the drug at one or both of its two hydroxyl groups.

In the CAT assay, two expression plasmids containing modified bacterial CAT genes were constructed. These plasmids were pC1000 and pC1007 as taught in Reynolds, M. A. "Triple-Strand-Farming methylphosphonate oligonucleotides targeted to mRNA efficiently block protein synthesis", *Proc Acad. Sci.* 91:12433–12437 at 12434 (1994), with the following modifications; the amplified DNA fragment contains the sequence target site for oligonucleotides 2519 (SEQ ID NO:6) or 2520 (SEQ ID NO:5) are substituted for the polypyrimidine insert. The two plasmids differed from one another by four bases in the translation initiation region targeted by the oligos. This gene is usually not found in eukaryotes; thus there is little or no background CAT activity in eukaryotic cells. Cell extracts are incubated with $^3H$ or $^{14}C$ chloramphenicol and n-butyryl coenzyme A. $^3H$ or $^{14}C$ chloramphenicol+n-butyryl coenzyme A—CAT→$^3H$ or $^{14}C$ chloramphenicol-n-butyryl. The modified chloramphenicol partitions into the xylene fraction while the unmodified chloramphenicol remains in the aqueous phase.

Cos 7 cells or A10 smooth muscle cells are plated the day before the experiment so that confluency is approximately 70% on the day of the experiment. Formulations of lipofectin complexed with plasmid and lipid constructs complexed with phosphorthioate oligonucleotides are diluted in OptiMEM, a serum-free medium. The cells are washed once with OptiMEM and then incubated for 3 hr with 0.5 mL of the diluted liposome-oligo complexes. The liposomes were removed and washed with OptiMEM and transfected for 3 hours with the target plasmid complexed with Lipofectin.

The plasmid complexes were removed and the cells were cultured overnight in complete medium. The cells were harvested approximately 16 hours after the addition of the target plasmid. Cell lysates were analyzed for CAT activity to assess inhibition and protein content. The results are shown in Table 3.

TABLE 3

Transiently Transfected COS 7 Cells

| Formulation | Lipid:oligo | % Inhib. 1 μM | 0.5 μM | 0.1 μM oligo |
|---|---|---|---|---|
| DOTAP:DOPE:Amch (1:1:0.5) | 5:1 | 94, 91 | 94 | 64 |
| DODAP:DOPE:Amch (1:1:0.5) | 5:1 | 92, 90 | 93 | 64 |
| DOPE:Amch (1:1) | 10:1 | 90 | 85 | 39 |
| DMPE:Amch (1:1) | 10:1 | 89 | 85 | 32 |
| DMPE:Amch (1:1) | 5:1 | 88, 95, 95 | 79 | 25 |
| DGE:DOPE:Amch (1:1:0.5) | 5:1 | 84, 90 | 50 | 11 |
| DMPE:Amch (1:1.5) | 10:1 | 88 | 72 | 29 |
| DMTAP:DMPE:Amch (1:1:0.5) | 5:1 | 92 | 83 | 24 |
| DMDAP:DMPE:Amch (1:1:0.5) | 5:1 | 84 | 50 | 15 |
| DMTAP:DMPE:Amch (1:1:1) | 5:1 | 87 | 70 | 41 |
| Lipofectin | 2.5:1 | 93, 86 | 90 | 62 |

A stably inducible model was also evaluated using COS 7 cells and A10 smooth muscle cells. These cells were stably transfected with a plasmid pC1041: modified chloramphenicol acetyl transferase (CAT) gene inserted into pMEP4 (Clonetech).

A modified chloramphenicol acetyl transferase (CAT) gene producing wild-type CAT protein was amplified in a PCR reaction using the following primer: 5' primer:

Hind III

---

5' cac agg ctt gtc gac tcg agt gca gga gct aag gaa gct acc atg gag aag aag atc act gga tat acc acc 3' (SEQ ID NO: 7)
3' primer:

---

Not I

5' tta tgc ggc cgc tta cgc ccc gcc ctg cca 3' (SEQ ID NO:8)
The amplified fragment was cut using Hind III and Not I restriction enzymes and ligated into Hind III/Not I cut pMEP4 (Clontech) vector. The amino terminal protein and 5' nucleotide sequences of the CAT gene in pC1041 compared to wild-type CAT are:

Wild-type CAT:
5'                                   +1                                         3'
                    Met Glu Lys Lys Ile Ser Gly Tyr Thr Thr (SEQ ID NO: 9)

uuu uca gga gcu aag gaa gcu aaa aug gag aaa aaa auc acu gga uau acc acc (SEQ ID NO: 10)

pG1041, UCAT:
5'                                   +1                                         3'
                    Met Glu Lys Lys Ile Ser Gly Tyr Thr Thr (SEQ ID NO: 11)

agu gca gga gcu aag gaa gcu acc aug gag aag aag auc acu gga uau acc acc (SEQ ID NO: 12)

The first adenosine is of the open reading frame is designated +1. The coding region nucleotide base changes between wild-type and pC1041 are conservative and do not change the amino acid sequence. Amino acid code: Asp=aspartic acid, Arg=arginine, Glu=glutamic acid, Gly=glycine, Ile=isoleucine, Lys=lysine, Met=methionine, Ser=serine, Thr=threonine, Tyr=tyrosine.

containing an inducible CAT gene using LipofectAmine (DOSPA:DOPE 3:1 mole ratio), and were plated the day before the experiment, treated with the liposomes and washed as described above. The liposome-oligo complexes were removed, washed in OptiMEM and cultured overnight in medium containing $CdCl_2$, which induces protein production. The cells are harvested approximately 16 hours later and analyzed for CAT activity. Cells were treated with μM oligo. The results are displayed in Tables 4 and 5.

TABLE 4

Stably Transfected COS7 Cells with PS Oligonucleotides

| Formulation | Lipid:Oligo Concentration | % Inhibition |
|---|---|---|
| DOTAP:DOPE:Amch (1:1:1) | 3.3:1 | 25% |
| DODAP:DOPE:Amch (1:1:1) | 3.3:1 | 20% |
| DOPE:Amch (1:1) | 5:1 | 0% |
| LipofectAmine | Not Reported | 59% |
| DOPE:Amch (1:1) | 5:1 | 22% |
| DOPE:Amch (1:1) | 1.25:1 | 16% |
| DOPE:Amch (1:1) | 0.5:1 | 1% |
| Lipofectin | Not Reported | 36% |
| LipofectAmine | Not Reported | 60% |
| DOTAP:DOPE:Amch (1:1:0.5) | 5:1 | 76% |
| DOPE:Amch (1:1) | 5:1 | 16% |
| LipofectAmine | 8:1 | 66% |
| DOPE:Amch (1:1.5) | 5:1 | 35% |
| DOTAP:DOPE:Amch (1.3:1:1.2) | 5:1 | 74% |
| DOTAP:DOPE:Amch (1:1:1.5) | 5:1 | 73% |

TABLE 5

Stably Transfected A10 Cells with PS Oligonucleotides

| Formulation | Lipid:Oligo Concentration | % Inhibition |
|---|---|---|
| DOPE:Amch (1:1.5) | 5:1 | 0% |
| LipofectAmine | 6:1 | 81% |
| DOTAP:DOPE:Amch (1.3:1:1.2) | 5:1 | 16% |
| DOTAP:DOPE:Amch (1:1:1.5) | 5:1 | 60% |
| LipfectAmine | 6:1 | 48% |
| DOPE:Amch (1:1.5) | 5:1 | 4% |

*Significant inhibition was observed in most formulas.

EXAMPLE 4

Figure 3A:
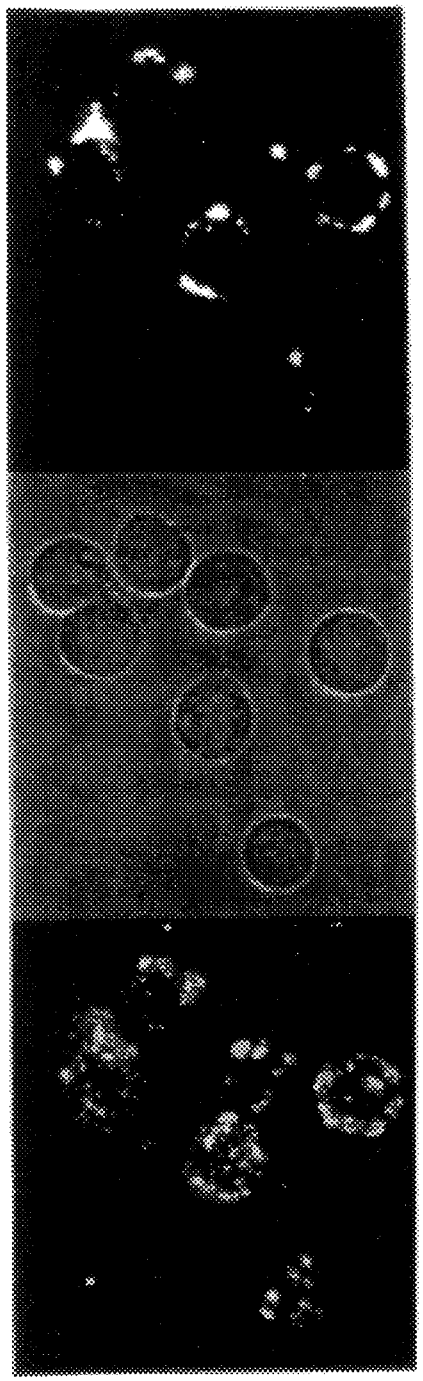
FIGS. 3A & 3B show a confocal micrograph of DOPE:Amch complexed with labeled chimeric oligonucleotide taken at 2.5 hours and 16 hours respectively.
Figure 3B:
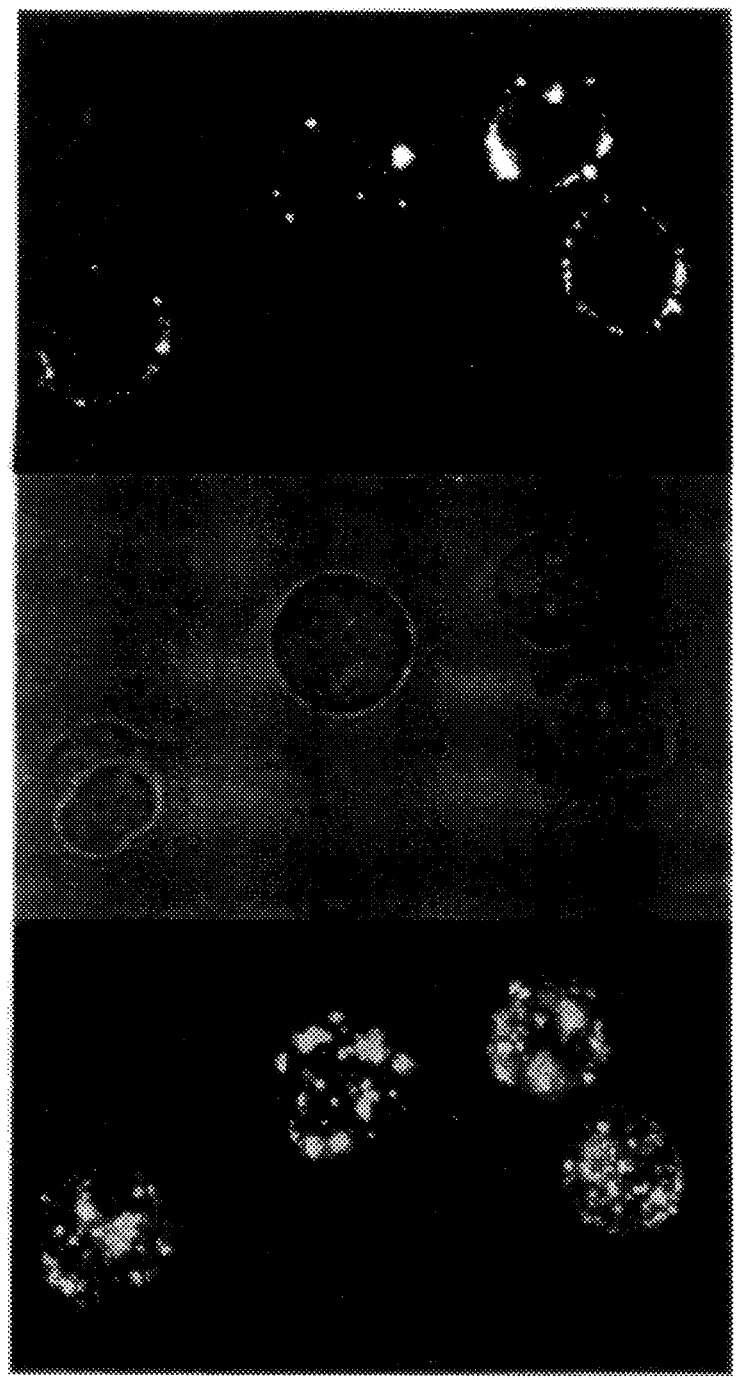
Figure 4A:
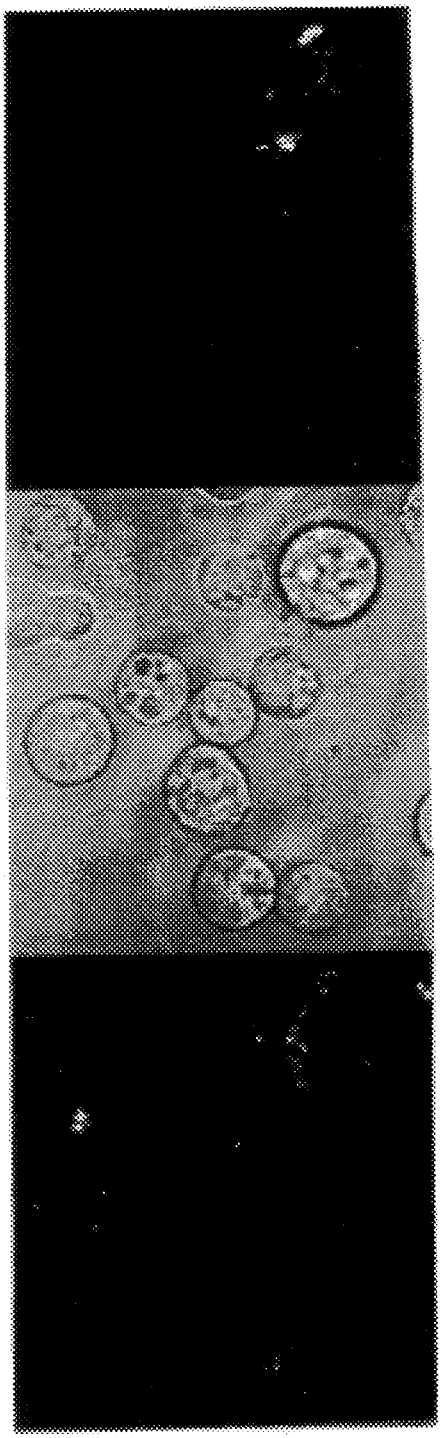
FIGS. 4A & 4B show a confocal micrograph of DSPC:Chol complexed with labeled chimeric oligonucleotide taken at 2.5 hours and 16 hours respectively.
Figure 4B:
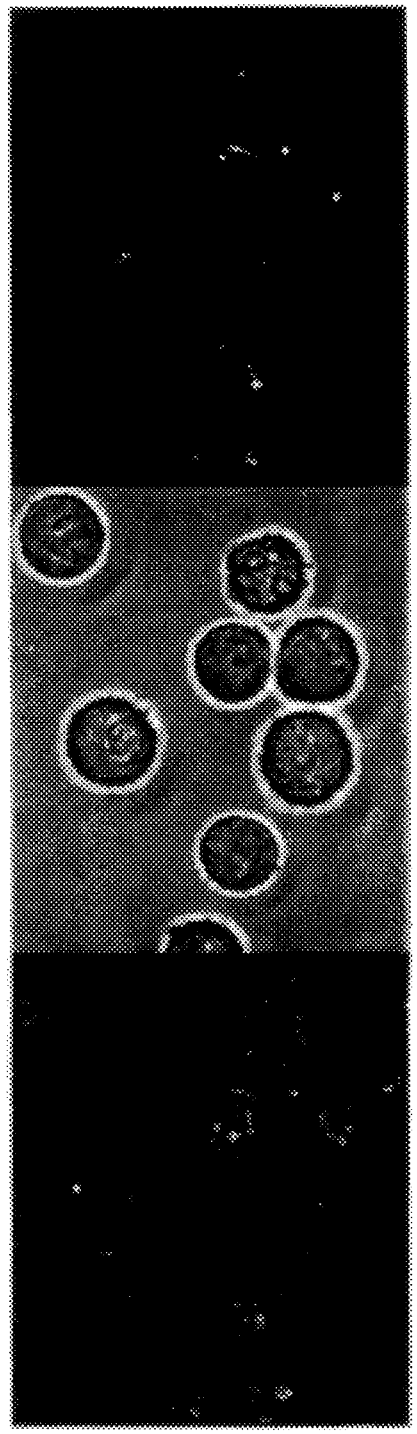

A confocal microscopy study was undertaken to further verify cytoplasmic delivery of oligonucleotides using lipid constructs comprised of aminomannose derivatized cholesterol, DOPE:Amch (1:1 molar ratio) and DSPC:chol (2:1 molar ratio) were prepared as in Examples 1 & 2. The DOPE:Amch lipid constructs were incubated for 10 minutes at 65° C. with a fluorescently labeled chimeric oligonucleotide having the sequence 5'-GGTATATCCAGTGATCTTCTTCTC-3' (SEQ ID NO:13). The lipid to oligonucleotide ratio was 5:1 w/w. DSPC:chol liposomes were prepared by hydrating the lipids with buffer containing the chimeric oligonucleotides and sonication. Six flasks containing $10^6$ P1798 (lympocaroma cells) cells in 10 ml complete Iscoves (10% Fetal Calf Serum, 1% penicillin/streptomycin) were incubated at 37° C., 5% $CO_2$. The cells were then incubated with 50 μg of oligonucleotide, either as free oligo or lipid associated oligo. Flasks 1, 2 and 3 were incubated with free oligo or oligo complexed with one of the two lipid formulations overnight (16 hour incubation). Flasks 4, 5 and 6 were incubated the next morning with free oligo or oligo complexed with one of the two lipid formulations (2.5 hour incubation). Cells were removed at 2.5 and 16 hours. The cells were washed to remove unassociated liposomes/oligonucleotide and examined by confocal microscopy. For each sample, a confocal microscopy series and corresponding bright field image were recorded. That is, a midsection flouresence (top), bright-field (middle) and 3-d reconstruction (bottom) are displayed in FIGS. 2–4. FIGS. 2A and 2B show rapid and intense flouresence diffusing from the edge of the cells into the cytoplasm. As the figures indicate, Amch:DOPE lipid constructs exhibit rapid and concentrated fluorescence into the cytoplasm as shown by intense fluorescence in the cytoplasm whereas the cells incubated with free oligonucleotide and oligonucleotide associated with DSPC:chol constructs shows very little fluorescence at all time periods.

EXAMPLE 5

A transfection study was carried out to further verify the ability of aminomannose derivatized cholesterol lipid constructs to deliver oligonucleotides into the nucleus of a cell. As noted above, LFA is currently used to transfect a plasmid, that is, introduce the plasmid into the nucleus of a cell so that it expresses a protein for which it codes. The plasmid was pC1035: Modified chloramphenicol acetyl transferase (CAT) gene inserted into pRc/CMV (Invitrogen).

A modified chloramphenicol acetyl transferase (CAT) gene producing wild-type CAT protein was amplified in a PCR reaction using the following primers:

5' primer:

Hind III

5' atc caa gct tcg acg aga ttt tca gga 3' (SEQ ID NO: 14)

3' primer:

Not I

5' tta tgc ggc cgc tta cgc ccc gcc ctg cca 3' (SEQ ID NO: 8)

The amplified fragment was cut using Hind III and Not I restriction enzymes and ligated into Hind III/Not I cut pRc/CMB (invitrogen) vector. The amino terminal protein and 5' nucleotide sequence of the CAT gene in pC1035 are:

Wild-type CAT:

+1                                              3'

Met Glu Lys Lys Ile Ser Gly Tyr Thr Th (SEQ ID NO: 9)

uuu uca gga gcu aag gaa gcu aaa aug gag aaa aaa auc acu gga uau acc acc (SEQ ID NO: 10)

It is known that LFA is optimized at a lipid:plasmid w/w ratio of 6:1. The following lipid:plasmid constructs were formed: DOPE:Amch (1:1 molar ratio) with a lipid plasmid ratio w/w of 10:1; DMPE:Amch (1:1 and 1:1.5 molar ratios) with lipid plasmid ratio w/w of 10:1; DODAP:DOPE:Amch (1:1:1) at lipid plasmid ratios w/w of 15:1 and 10:1. The DOPE:Amch lipid constructs were 1.14 times more efficacious then LFA. The DMPE:Amch constructs, 1:1 and the 1:1.5, were 0.44 and 0.71 as effective as LFA respectively. The DODAP:DOPE:Amch 15:1 and 10:1 formulas, were 0.02 and 0.01 as effective as the LFA respectively. In all cases, the aminomannose constructs were effective in transfecting A10 smooth muscle cells.

EXAMPLE 6

Lipid constructs were formulated as in Example 2 using the following Oligonucleotides: cdc gene (rat) GTCCTC-CATAGTTACTCA (SEQ ID NO:1); PCNA gene (rat) GAT-CAGGCGTGCCTCAAA (SEQ ID NO:2); rev-AS (2328) ACTCATTGATACCTCCTG (SEQ ID NO:3); rev-AS (2342) AAACTCCGTGCGGACTAG (SEQ ID NO:4). Ten unheparinized rats were treated with 10 µM total oligo (antisense or reverse antisense) complexed with DOPE:aminomannose (1:1) at a 5:1, 1.25:1 or 0.5:1 lipid:oligo w/w ratios and sacrificed 2 weeks post-angioplasty. Eight heparinized rats were treated with 10 µM total oligo (antisense or reverse antisense) complexed with DOPE:aminomannose liposomes (1:1) at 5:1 lipid:oligo w/w ratio and sacrificed 2 weeks post-angioplasty.

A No. 2 French Fogarty catheter was used to induce vascular injury in male Spraque-Dawley rats. The rats were anesthetized, and a cannula introduced into the left common carotid via the external carotid artery. After vascular injury of the common carotid, the distal injured segment was transiently isolated by temporary ligatures. The formulation (0.25 ml) containing the antisense oligos (5 µM of each) was infused into the segment and incubated for 15–30 minutes at room temperature. Control rats received an identical formulation containing reverse antisense oligos (rev-AS). Following incubation, the infusion cannula was removed and blood flow to the common carotid restored by release of the ligatures. At 2 weeks after catheterization, rats were s sacrificed and vessels perfused-fixed with 4% paraformaldehyde. Sections were analyzed for neointima formation, and data expressed as neointimal/medial area ratios and percent inhibition.

Unheparinized rats treated with DOPE:aminomannose lipid constructs formulated at 1.25:1 or 0.5:1 lipid:oligo w/w showed excellent inhibition of neointima formation as compared to rats treated with liposomes formulated with reverse antisense. Neointima formation was inhibited approximately 45% and 38% by the 0.5:1 and 1.25:1 constructs respectively. However, liposomes formulated with 5:1 lipid:oligo w/w were not effective. 60–70% of the unheparinized rats showed moderate to severe thrombosis. Heparinized rats treated with the 5:1 constructs showed no thrombosis and no reduction in neointima formation when compared to heparinized rats treated with reverse antisense.

EXAMPLE 7

Lipid constructs were prepared as in Example 2 and complexed with oligonucleotides as in Example 6. Rats were heparinized and treated with constructs complexed with cdc2 and PCNA (0.5:1 lipid:oligo w/w and 50 µM oligo, 0.5:1 lipid:oligo w/w and 5 µM oligo, 0.25:1 lipid:oligo w/w and 5 µM oligo) or reverse cdc2 and PCNA (0.5:1 lipid:oligo w/w and 5 µM oligo) phosphorothioate oligonucleotides. The results of the study are listed below in Table 1. Unlike the previous study done with unheparinized rats (Example 1), only 1 rat in the entire study showed signs of thrombosis (rat treated with 0.25:1 lipid:oligo w/w and 5 µM oligo). All rats treated with antisense oligonucleotides showed a therapeutic response (treated arteries as compared to untreated control arteries).

TABLE 6

Neointima Formation in Treated vs. Untreated Control Arteries

| Treatment Group | Treated | Untreated | % Reduction | t-test |
|---|---|---|---|---|
| AS 0.5:1, 50 µM | 0.179 ± 0.035 | 0.234 ± 0.042 | 22.9% | 0.013 |
| AS 0.5:1, 5 µM | 0.153 ± 0.044 | 0.250 ± 0.053 | 38.7% | <10$^{-4}$ |
| AS 0.25:1, 5 µM | 0.158 ± 0.028 | 0.257 ± 0.034 | 38.5% | <10$^{-4}$ |
| rev AS 0.5:1, 5 µM | 0.181 ± 0.022 | 0.183 ± 0.018 | None | 0.834 |

EXAMPLE 8

Oligonucleotides stock solution were prepared as followed: antisense, c-myc:5'-AACGTTGAGGGGCAT-3' (SEQ ID NO:15) and nonsense c-myc:5'-CTGAAGTGGCATGAG-3' (SEQ ID NO:16) were dissolved in phosphate buffer to make a stock solution having a concentration of approximately 3.4 mg/ml. A lipid film was prepared containing hydrogenated soy phosphatidylcholine:chol:Amch in a mole ratio of 16:8:1 having a total lipid concentration of 560 milligrams. One ml of the oligonucleotide stock solution was added to the lipid film and bath sonicated at a temperature of 40° C. for 10 seconds. The resulting solution was put through a 4 cycle freeze-thaw procedure using liquid nitrogen. The resulting homogeneous solution is extruded first through a 0.8 µM filter membrane (3 times) then extruded through a 0.45 µM filter (3 times) and finally extruded through a 0.2 µM filter (3 times). The free oligonucleotides were removed by passing through a Sephadex G-50 column with a bed volume of about 18 ml. The vesicle volume was recovered in 5.5 ml of buffer. Control liposomes were prepared as above without oligonucleotides. The mean diameter of the control liposomes was 80.0±38.4 nm. The mean diameter of the oligonucleotides containing liposomes were 210±80 nm. The antisense c-myc and oligonucleotides concentration was 50 µg/ml.

The liposomes containing oligonucleotides were tested against two strains of small cell lung carcinoma. The first line is a cisplatin (cDDP), sensitive line (GLC4) and the second line a 5.6× cDDP resistant sub-line (GLC4-cDDP). In GLC4 and GLC4-cDDP there is a 40–60× c-myc oncogene amplification with a corresponding c-myc mRNA and protein overexpression. The lipid concentration in the control group was 21.8 mg/ml and the lipid concentration in the liposome preparation containing the oligonucleotides was 10.3 mg/ml. Both cell lines show growth inhibition after incubation with 10 and 20 µM antisense c-myc oligonucleotides in SCLC-medium, a defined serum-free culture medium (heat-inactivated for 1 hour at 70° C.). Thus, the remaining nucleases were heat-inactivated. In these cell cultures nonsense oligonucleotides do not have any inhibitory effect. The results were listed in Table 7. The results in Table 7 disclose that encapsulated oligonucleotides in liposomes allow for a 10 to 20 times reduction of antisense c-myc oligonucleotides concentration needed to exert the same inhibitory effect in the GLC4 and GLC4-cDDP cell lines compared to the unencapsulated antisense c-myc oligonucleotides. Empty liposomes and nonsense oligonucleotides did not have an inhibitory effect.

TABLE 7

| % Growth to control ± sd (n = 3) | GLC 4 | GLC4-cDDP |
|---|---|---|
| control | 100 | 100 |
| 10 μM as c-myc n-ODN | 83.6 ± 5.9 | 82.1 ± 7.9 |
| 20 μM as c-myc n-ODN | 69.5 ± 10.2 | 55.5 ± 5.9 |
| 10/20 μM ns c-myc n-ODN | 99.7 ± 6.1 | 100.3 ± 6.1 |
| 1 μM as c-myc in liposomes | 70.3 ± 9.0 | 62.1 ± 8.6 |
| 2.5 μM as c-myc in liposomes | 56.9 ± 10.3 | 31.3 ± 15.5 |
| empty liposomes | 104.6 ± 8.3 | 80.4 ± 14.6 |

While the invention has been described with reference to specific embodiments and examples, it will be appreciated that various changes and modifications can be made without departing from the invention.

Although this specification has been disclosed and illustrated with reference to particular applications, the principles involved are susceptible to numerous other applications which will be apparent to those skilled in the art. The invention is, therefore, to be limited only as indicated by the scope of the appended claims.

I claim:

1. A method of targeting vascular smooth muscle tissue by delivering to an artery a lipid construct containing a therapeutic or imaging agent wherein said construct comprises an aminomannose derivatized cholesterol.

2. The method as recited in claim 1 wherein the aminomannose derivatized cholesterol comprises 6-(cholest-5-en-3β-yloxy)hexyl-6-amino-6-deoxy-1-thio-α-D-mannopyranoside.

3. The method of claim 2 wherein the therapeutic agent comprises an agent which prevents neointima formation.

4. The method of claim 3 wherein the method of delivering said construct comprises a percutaneous transluminal coronary angioplasty procedure.

5. The method of claim 2 wherein the method of delivering said construct comprises a percutaneous transluminal coronary angioplasty procedure.

6. The method of claim 1 wherein the therapeutic agent comprises an agent which prevents neointima formation.

7. The method of claim 3 wherein the method of delivering said construct comprises a percutaneous transluminal coronary angioplasty procedure.

8. The method of claim 1 wherein the method of delivering said construct comprises a percutaneous transluminal coronary angioplasty procedure.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

GTCCTCCATA GTTACTCA    18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

GATCAGGCGT GCCTCAAA    18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

ACTCATTGAT ACCTCCTG                                           18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AAACTCCGTG CGGACTAG                                           18

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:5:

TAGCTTCCTT AGCTCCTGCA T                                       21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

TAGCTTCCGC AACTCTTGCA T                                       21

( 2 ) INFORMATION FOR SEQ ID NO:7:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

```
CACAAGCTTG TCGACTCGAG TGCAGGAGCT AAGGAAGCTA CCATGGAGAA GAAGATCACT    60

GGATATACCA CC                                                        72
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

```
TTATGCGGCC GCTTACGCCC CGCCCTGCCA                                     30
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

```
Met Glu Lys Lys Ile Ser Gly Tyr Thr Thr
 1           5                        10
```

( 2 ) INFORMATION FOR SEQ ID NO:10:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:10:

```
UUUUCAGGAG CUAAGGAAGC UAAAAUGGAG AAAAAAAUCA CUGGAUAUAC CACC          54
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:11:

Met  Glu  Lys  Lys  Ile  Ser  Gly  Tyr  Thr  Thr
    1                        5                            10

( 2 ) INFORMATION FOR SEQ ID NO:12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:12:

AGUGCAGGAG CUAAGGAAGC UACCAUGGAG AAGAAGAUCA CUGGAUAUAC CACC        54

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

GGTATATCCA GTGATCTTCT TCTC        24

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

ATCCAAGCTT CGACGAGATT TTCAGGA        27

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:15:

AACGTTGAGG GGCAT                                                                               15

( 2 ) INFORMATION FOR SEQ ID NO:16:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

CTGAAGTGGC ATGAG                                                                               15